United States Patent
Bissinger et al.

(10) Patent No.: US 6,624,236 B1
(45) Date of Patent: Sep. 23, 2003

(54) CYCLOSILOXANE-BASED CROSS-LINKABLE MONOMERS, PRODUCTION THEREOF AND USE THEREOF IN POLYMERIZABLE MATERIALS

(75) Inventors: Peter Bissinger, Diessen (DE); Oswald Gasser, Seefeld (DE); Rainer Guggenberger, Herrsching (DE); Wolfgang Soglowek, Diessen-Obermulhausen (DE); Gunther Eckhardt, Bad Dürrenberg (DE)

(73) Assignee: 3M Espe AG, Seefeld (DE)

( * ) Notice: Subject to any disclaimer, the term of this patent is extended or adjusted under 35 U.S.C. 154(b) by 0 days.

(21) Appl. No.: 09/868,450

(22) PCT Filed: Dec. 22, 1999

(86) PCT No.: PCT/EP99/10318

§ 371 (c)(1),
(2), (4) Date: Sep. 19, 2001

(87) PCT Pub. No.: WO00/42092

PCT Pub. Date: Jul. 20, 2000

(30) Foreign Application Priority Data

Dec. 24, 1998 (DE) .......................................... 198 60 361

(51) Int. Cl.⁷ ............................................... C08L 83/04
(52) U.S. Cl. ........................... 524/588; 528/32; 528/31; 528/37; 528/34; 528/27; 556/458; 556/460; 556/457; 525/479; 523/109; 526/279

(58) Field of Search ............................. 528/32, 31, 37, 528/34; 556/458, 460, 457; 525/479; 523/109; 526/279; 524/588

(56) References Cited

U.S. PATENT DOCUMENTS 5,233,006 A * 8/1993 Wolter et al.

FOREIGN PATENT DOCUMENTS

| DE | A1-3741575 | 6/1988 |
|----|------------|--------|
| DE | A1-3838587 | 5/1990 |
| DE | A1-19648283 | 5/1998 |
| EP | A2238025 | 9/1987 |
| EP | A2381961 | 8/1990 |
| EP | A1475437 | 3/1992 |

* cited by examiner

*Primary Examiner*—Robert Dawson
*Assistant Examiner*—Kuo-Liang Peng
(74) *Attorney, Agent, or Firm*—Birch, Stewart, Kolasch & Birch, LLP

(57) ABSTRACT

The invention relates to polysiloxanes from cross-linkable monomers based on cyclosiloxanes and their use in polymerizable compositions. The invention relates in particular to polysiloxanes from sol-gel-condensable cyclosiloxane (meth)acrylates as well as resinous compositions, obtainable by hydrolytic condensation of one or more hydrolyzable and condensable cyclosiloxane(meth)acrylates.

12 Claims, No Drawings

CYCLOSILOXANE-BASED CROSS-LINKABLE MONOMERS, PRODUCTION THEREOF AND USE THEREOF IN POLYMERIZABLE MATERIALS

This application is the national phase under 35 U.S.C. §371 of PCT International Application No. PCT/EP99/10318 which has an International filing date of Dec. 22, 1999, which designated the United States of America and was not published in English.

The invention relates to polysiloxanes from cross-linkable monomers based on cyclosiloxanes and their use in polymerizable compositions. The invention relates in particular to polysiloxanes from sol-gel-condensable cyclosiloxane(meth)acrylates as well as resinous compositions, obtainable by hydrolytic condensation of one or more hydrolyzable and condensable cyclosiloxane(meth)acrylates.

STATE OF THE ART

Non-cyclic sol-gel-condensable siloxanes as well as polycondensates based on hydrolytically condensable siloxanes for use in the surface coating field are already known from EP-O 450 624-A2. Due to the structure of these compounds, they are particularly suitable for the preparation of coating materials, adhesives and sealing compounds.

Silicic acid (hetero)polycondensates which are modified with organic groups, as well as processes for their preparation, are already known in large numbers (DE-A-38 35 968, DE-A-40 11 045). Such condensates are used for the most varied purposes, for example as moulding compounds, surface coatings and coverings.

Condensable monomeric cyclic siloxanes are known from EP-A-0 475 437. Within the framework of the teaching this document, the siloxanes described are not condensed, but are used as coupling agents.

Due to the wide-ranging possible applications of this substance class, there is a constant demand for the modification of the already-known compounds in order to open up new fields of application and to optimize their properties for particular purposes.

In the field of dentistry, there is in particular the demand for low-shrinkage compositions curable by radical polymerization with good physical parameters such as bending and compressive strength and hardness. There is also a constant demand for mixtures which have a toxicologically acceptable amount of residual monomers. i.e. monomers which are not incorporated into the polymerized network.

OBJECT

The object of the invention is to provide a new class of polymers which are particularly suitable for use in the dental field. It is also to be possible to prepare from the corresponding monomers resinous compositions which—optionally in the presence of initiators—can be cured photochemically, thermally or chemically.

ACHIEVEMENT

This object is achieved according to the invention by polysiloxanes based on cyclic siloxanes which have sol-gel-condensable groups and simultaneously radically polymerizable groups and thus make possible an incorporation into a three-dimensional network of filling substances, which are optionally surface-treated, and optionally of further reactive monomers.

Unusually and surprisingly, it is the fact that, despite the generally low viscosity of the siloxanes used as starting substances, compositions with high compressive and bending strength can be obtained.

The use of cyclic-inorganic, in contrast to linear or branched organic compounds, is advantageous because, amongst other things, these produce a relatively little compressible, chemically stable network. The substituents on the central ring structure are evenly orientated in the spatial direction, which leads to an extremely homogeneous network. Fracture points can thereby be avoided.

Particularly interesting properties can be obtained through co-condensates of the monomers according to the invention based on cyclosiloxanes with organic monomers which are described for example in EP-0-450 624-A2. In particular, the degree of cross-linking of the cured, radically polymerized material can be increased.

Such co-condensates can be understood as co- and terpolymers of hydrolysates (leads to randomized co- and terpolymers) or pre-condensates (leads to block co- and terpolymers) of representatives of the formulae (1) with (2) as well as (7), (8) or (9). Both possibilities are meant herein. These co- and tercondensates obey the general formula (1a) mentioned later.

DEFINITIONS

In the following, the definitions to be understood within the framework of this invention are given for the terms alkyl or alkyl radical, alkenyl or alkenyl radical and aryl or aryl radical.

Straight-chained, branched or cyclic radicals with 1 to 20, preferably 1 to 10 carbon atoms and preferably low alkyl radicals with 1 to 6, preferably 1 to 4 carbon atoms for example are conceivable for alkyl.

Particularly preferred alkyl radicals in general are linear or branched or cyclic radicals, such as methyl, ethyl, n-propyl, isopropyl, n-butyl, sec-. butyl, isobutyl, n-pentyl, n-hexyl, cyclohexyl, 2-ethylhexyl, dodecyl, octadecyl.

Straight-chained, branched or cyclic radicals with 2 to 20, preferably 2 to 10 carbon atoms and preferably low alkenyl radicals with 2 to 6 carbon atoms for example are conceivable as alkenyl radicals.

Preferred alkenyl radicals are linear or branched or cyclic radicals, such as vinyl, allyl and 2-butenyl.

Aryl radicals are to be understood as those with 6 to 18, preferably 6 to 12 C atoms. Preferred definitions for aryl radicals are phenyl, biphenyl and naphthyl.

Alkoxy, acyloxy, alkylamino, dialkylamino, alkylcarbonyl, alkoxycarbonyl, arylalkyl, alkylaryl, alkylene, arylene and alkylenearylene radicals mentioned in the course of the invention are preferably derived from the alkyl and aryl radicals named above.

Special examples are methoxy, ethoxy, n- and i-propoxy, n-, i-, sec.- and tert-butoxy, monomethylamino, monoethylamino, dimethylamino, diethylamino, n-ethylanilino, acetyloxy, propionyloxy, methylcarbonyl, ethylcarbonyl, methoxycarbonyl, ethoxycarbonyl, benzyl, 2-phenylethyl and tolyl.

All named radicals can optionally carry one or more substituents, for example, halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, ercapto, cyano, nitro, epoxy, $SO_3H$ or $PO_3H_2$.

Fluorine, chlorine and bromide and in particular chlorine are preferred as halogens.

DETAILED DESCRIPTION OF THE INVENTION

The polysiloxanes according to the invention can be obtained by sol-gel condensation of A1. 60 to 100 mol.-%, relative to the condensate from A1, A2 and A3, monomers or precondensates of sol-gel-condensable cyclic siloxanes of the general formula (1),

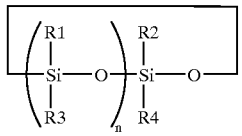
(1)

in which the variables are defined as follows:
R$^1$, R$^2$: alkyl with 1 to 10, preferably 1 to 5 C atoms, alkenyl with 1 to 10, preferably 1 to 5 C atoms, fluoroalkyl with 1 to 10, preferably 1 to 5 C atoms, cycloalkyl with 3 to 12, preferably 5 to 12 C atoms, aryl with 6 to 18, preferably 6 to 12 C atoms,
R$^3$: R$^5$—Z
R$^4$: R$^6$—(A—R$^6$)$_c$—SiX$_a$R$^7_b$,
R$^5$, R$^6$: alkylene linear or branched with 1 to 10, preferably 2 to 6 C atoms, alkenylene linear or branched with 1 to 10, preferably 2 to 6 C atoms, cycloalkylene with 3 to 12, preferably 5 to 8 C atoms, cycloalkenylene with 3 to 12, preferably 5 to 8 C atoms, alkarylene with 6 to 18, preferably 6 to 12 C atoms with up to 3 heteroatoms from the group O, N, S,
R$^7$: alkyl with 1 to 10, preferably 1 to 5 C atoms, alkenyl with 1 to 10, preferably 1 to 5 C atoms, aryl with 6 to 18, preferably 6 to 12 C atoms, alkylaryl with 6 to 24, preferably 6 to 18 C atoms, arylalkyl with 6 to 24, preferably 6 to 18 C atoms,
Z: a linear, branched or cyclic organic radical with at least one C=C double bond or at least one epoxide function and at least 4 to 50 carbon atoms and up to 10 heteroatoms from groups O, N and S, Z preferably being OC(O)CH=CH$_2$, OC(O)C(Me)=CH$_2$, vinylcyclopropyl, norbornenyl, oxetanyl, 3,4-epoxycyclohexyl and alkenyl linear or branched with 1 to 20, preferably 2 to 6 C atoms,
A: O, S, NHC(O)O, NHC(O)NR$^8$, OC(O)NH, OC(O), C(O)O,
X: H, halogen, hydroxy, acyloxy, alkylcarbonyl, NR$^8_2$, alkoxy, alkoxycarbonyl, the acyl, alkyl and alkoxy radicals containing 1 to 10, preferably 1 to 6 C atoms,
R$^8$: H, alkyl with 1 to 10, preferably 1 to 7 C atoms, aryl with 6 to 18, preferably 6 to 12 C atoms,
n: 2 to 16, preferably 2 to 10,
a: 1, 2 or 3,
b: 0, 1 or 2,
with the proviso that a+b=3, and
c. 0 or 1,
A2. 0 to 40 mol.-%, relative to the condensate from A1, A2 and A3, of organic sol-gel-condensable monomers, and
A3. 0 to 40 mol.-%, relative to the condensate from A1, A2 and A3, of one or more sol-gel-condensable compounds of silicon and optionally other elements from the group B, Al, P, Sn, Pb, the transition metals, the lanthanides and aktinides,
where the sum of the amounts of A2 and A3 may not exceed 40 mol.-% and the amounts of A1, A2 and A3 must be made up of 100 mol.-%.

In a preferred version, the polysiloxanes can be obtained by sol-gel condensation of 100 mol.-% component A1.

The sol-gel-condensation takes place, optionally in the presence of catalysts and/or solvents, through the action of water or moisture in amounts of 1 to 100, preferably 5 to 100 mol percent, relative to the monomeric sol-gel-condensable cyclic siloxanes according to formula (1).

A further subject of the invention are resinous compositions which can be photchemically, thermally or chemically cured optionally in the presence of initiators, based on polymerizable polysiloxanes.

The resultant resins are the co- and terpolymers already mentioned above of the general formula (1a):

$$(A1)_{a1}(A2)_{a2}(A3)_{a3} \qquad (1a)$$

in which:
a1=60 to 100 mol-%,
a2=0 to 40 mol-%,
a3=0 to 40 mol-%,
with the proviso that the sum of a1, a2 and a3 must not exceed 40 mol-%.

A precondition given here for the presence of co- or terpolymers is that the components A1, A2 or A3 are covalently bound to each other, which is achieved according to the invention by at least partial co-condensation of the hydrolysis product or precondensates.

Another subject of the invention is furthermore resins which are produced by partial or complete hydrolysis of the groups X of representatives of the general formula (1) and subsequent partial or complete condensation with optional partial or complete saturation of the remaining Si—OH groups with R$^9$R$^{10}$R$^{11}$Si-groups, R$^9$, R$^{10}$ and R$^{11}$ standing for the same or different alk(en)yl groups with 1 to 10, preferably 1 to 6 C atoms.

Co-condensates of the partially or completely hydrolyzed representatives of the general formula (1) with representatives of the formula class A3, for example Si-, Ti- or Zr-alkoxides and/or substituted monoalkyltrialkoxysilanes also form a subject of the invention. Special examples of these follow later.

A subject of the invention are also polysiloxanes obtainable by sol-gel condensation of
A1. 60 to 100 mol.-%, relative to the condensate from A1 and A2, monomers or precondensates of the sol-gel-condensable cyclic siloxanes according to formula (1) and
A2. 0 to 40 mol.-%, relative to the condensate from A1 and A2, organic sol-gel-condensable monomers,
where the representatives of component A2 obey formula (2):

$$\{Y_eR_fSi[R'(B)_g]_{(4-e-f)}\}_xC \qquad (2)$$

in which the radicals and the indices have the following meaning:
Y: hydrogen, halogen, hydroxy, alkoxy, acyloxy, alkylcarbonyl, alkoxycarbonyl or —NR—$_2$;
R: alkyl, alkenyl, aryl, alkylaryl or arylalkyl;
R': alkylene, arylene or alkylenearylene:
R": hydrogen, alkyl or aryl;
B: O, S, PR", POR", NHC(O)O or NHC(O)NR";
C: linear or branched or cyclic or polycyclic organic radical, which contains at least one C=C double bond, consists of 3 to 70, preferably 3 to 50 carbon atoms and contains 0 to 20, preferably 0 to 10 heteroatoms from the group O, N, S; preferred are acryloyl, methacryloyl, acryloxy-eth-2-yl, methacryloxy-eth-2-yl, 5-acryloyl-3-oxa-hept-1-yl, 6-methacryloyl-3-oxa-hept-1-yl, pentaerythritol-triacrylate-prop-3-yl ether, pentaerythritol-trimethacrylate-prop-3-yl ether, di-pentaerythritol-pentaacrylate-prop-3-yl ether, di-pentaerythritol-pentamethacrylate-prop-3-yl ether, trimethylolethane-diacrylate-prop-3-yl ether, trimethylolethane-dimethacrylate-prop-3-yl ether, 1,2-propanediol-acrylate-prop-3-yl ether, 1,2-propanediol-methacrylate-prop-3-yl ether, 1,3-propanediol-acrylate-prop-3-yl ether, 1,3-propanediol-methacrylate-prop-3-yl ether, 1,3-butanediol-acrylate-prop-3-yl ether, 1,3-butanediol-methacrylate-prop-3-yl ether, 1,4-butenediol-acrylate-prop-3-yl ether, 1,4-butenediol-methacrylate prop-3-yl ether, 1,4-butinediol-acrylate-prop-3-yl ether, 1,4-butinediol-methacrylate-prop-3-yl ether, 1,5-pentanediol-acrylate-prop-3-yl ether, 1,5-pentanediol-methacrylate-prop-3-yl ether, 1,6-hexanediol-acrylate-prop-3-yl ether, 1,6-hexanediol-methacrylate-prop-3-yl ether, 1,8-octanediol-acrylate-prop-3-yl ether, 1,8-octanediol-methacrylate-prop-3-yl ether, 1,9-nonanediol-acrylate-prop-3-yl ether, 1,9-nonanediol-methacylate-prop-3-yl ether, 1,10-decanediol-acrylate-prop-3-yl ether, 1,10-decanediol-methacrylate-prop-3-yl ether, 1,12-dodecanediol-acrylate-prop-3-yl ether, 1,12-dodecanediol-methacrylate-prop-3-yl ether, glycerol-diacrylate-prop-3-yl ether, glycerol-dimethacrylate-prop-3-yl ether, 1,2,4-butanetriol-diacrylate-prop-3-yl ether, 1,2,4-butanetriol-dimethacrylate-prop-3-yl ether, 1,2,6-hexanetriol-diacrylate-prop-3-yl ether, 1,2,6-hexanetriol-dimethacrylate-prop-3-yl ether, diglycerol-triacrylate-prop-3-yl ether, diglycerol-trimethacrylate-prop-3-yl ether, erythritol-triacrylate-prop-3-yl ether, erythritol-trimethacrylate-prop-3-yl ether, mannitol-pentaacrylate-prop-3-yl ether, mannitol-pentamethacrylate-prop-3-yl ether, sorbitol-pentaacrylate-prop-3-yl ether, sorbitol-pentamethacrylate-prop-3-yl ether, inositol-pentaacrylate-prop-3-yl ether, inositol-pentamethacrylate-prop-3-yl ether, 2,4,-diacryloyl-3,5-triazine-6-(prop-3-yl), 2,4,-imethacryloyl-3,5-triazine-6-(prop-3-yl), (4-acryloxyphenyl)-(4-(prop-3-yl)phenyl)-sulfone, (4-methacryloxyphenyl)-(4-(prop-3-yl)phenyl)-sulfone, (4-acryloxy-phenyl)-(4-(prop-3-yl)phenyl)-ketone, (4-methacryloxyphenyl)-(4-(prop-3-yl)phenyl)-ketone, (4-acryloxyphenyl)-(4-(prop-3-yl)phenyl)-methane, (4-methacryloxyphenyl)-(4-(prop-3-yl)phenyl)-methane, 1(4-acryloxyphenyl)-1-(4-(prop-3-yl)phenyl)-ethane, 1(4-methacryloxyphenyl)-1-(4-(prop-3-yl)phenyl)-ethane, 2(4-acryloxyphenyl)-2(4-(prop-3-yl)phenyl)-propane, 2(4-methacryloxyphenyl)-2(4-(prop-3-yl)phenyl)-propane, 2(4-acryloxyphenyl)-2(4-(prop-3-yl)phenyl)-perfluoropropane, 2(4-methacyloxyphenyl)-2(4-(prop-3-yl)phenyl)-perfluoropropane, 2(4-acryloxy-3,5-dibromophenyl)-2(4-(prop-3-yl)-3,5-dibromophenyl)-propane, 2(4-methacryloxy-3,5-dibromophenyl)-2(4-(prop-3-yl)-3,5-dibromophenyl)-propane, 3(4-acryloxyphenyl)-3(4-(prop-3-yl)phenyl)-pentane, 3(4-methacryloxyphenyl)-3(4-(prop-3-yl)phenyl)-pentane, 4(4-acryloxyphenyl)-4(4-(prop-3-yl)phenyl)-heptane, 4(4-methacryloxyphenyl)-4(4-(prop-3-yl)phenyl)-heptane, 1(4-acryloxyphenyl)-1 (4-(prop-3-yl)phenyl)-cyclopentane, 1(4-methacryloxyphenyl)-1(4-(prop-3-yl)phenyl)-cyclopentane, 1(4-acryloxyphenyl)-1 (4-(prop-3-yl)phenyl)-cyclohexane, 1(4-methacryloxyphenyl)-1(4-(prop-3-yl)phenyl) cyclohexane, 1(4-acryloxyphenyl)-1(4-(prop-3-yl) phenyl)-3,3,5-trimethylcyclohexane, 1(4-methacryloxyphenyl)-1(4-(prop-3-yl)phenyl)-3,3,5-trimethylcyclohexane, 1,1-bis(4-acryloxyphenyl)-1(4-(prop-3-yl)phenyl)-ethane, 1,1 -bis(4-methacryloxyphenyl)-1(4-(prop-3-yl)phenyl)-ethane, acryloxy-(prop-3-yl)-tricyclo[$5.2.1.0^{2.6}$]-decane, methacryloxy-(prop-3-yl)-tricyclo[$5.2.1.0^{2.6}$]decane;

e: 1, 2 or 3;

f: 0, 1 , or 2;

g: 0 or 1;

x: an integer, the maximum value of which corresponds to the amount of double bonds in the compound C minus 1 or is equal to the amount of double bonds in the compound C, if g=1 and B stands for NHC(O)O or NHC(O)NR".

Furthermore, the use of resins and/or the non-condensed compounds, in particular in dental compositions, is a subject of the invention.

The following monomers are preferred:

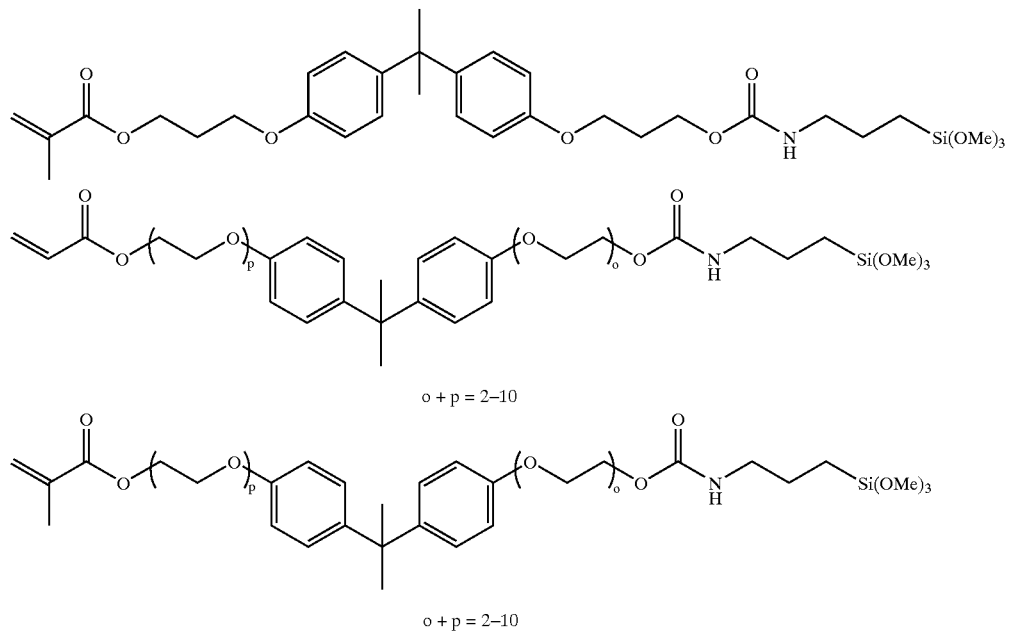

o + p = 2–10 o + p = 2–10

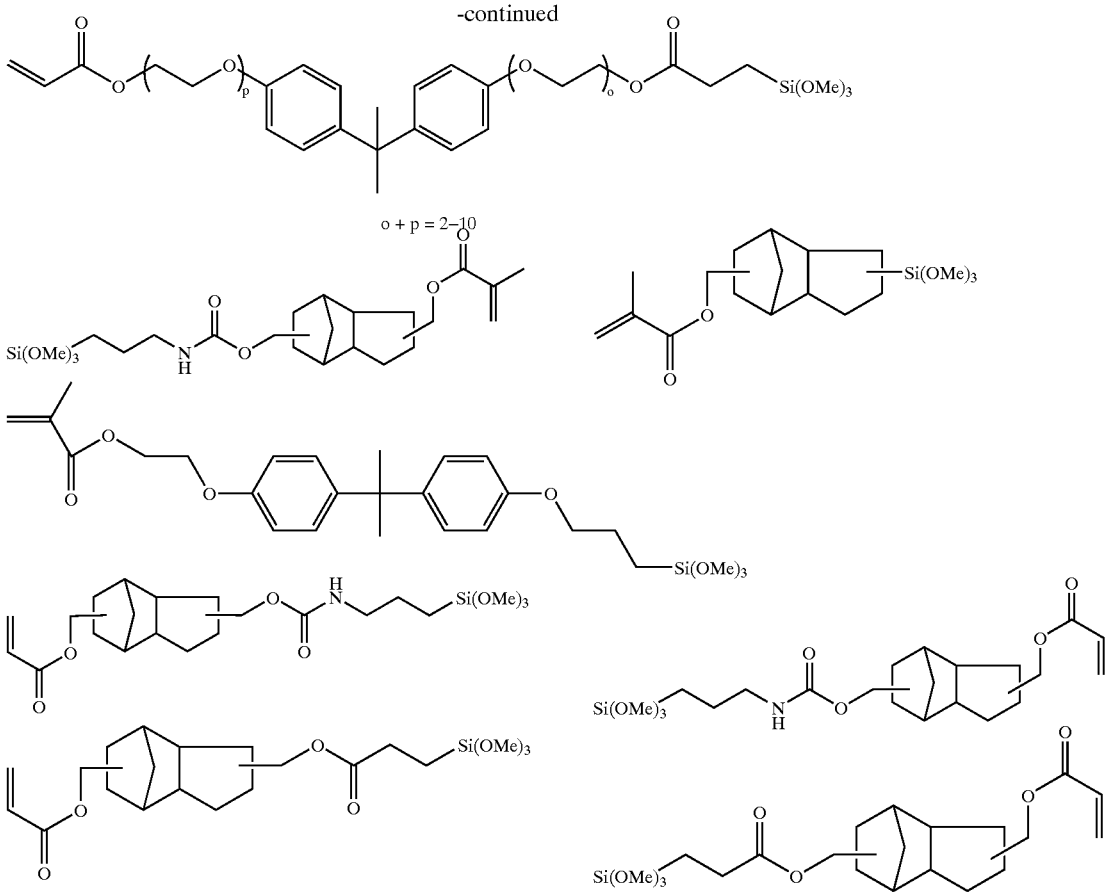

The starting point for the preparation of the sol-gel-condensable monomers according to the invention is generally cyclosiloxanes of formula (3):

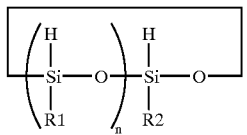
(3)

with $R^1$ and $R^2$ having the same meaning as in formula (1), which are reacted, accompanied by catalysis, substoichiometrically with compounds of formula (4):

$$R^{12}-(AR^6)_c-SiX_aR^7_b$$

with $R^{12}$ equal to alkenyl or alkinyl linear or branched with 1–10, preferably 2–6 C atoms, or cycloalkenyl or cycloalkinyl with 3–12, preferably 5–8 C atoms with up to 3 heteroatoms O, N, S and with the proviso that the other radicals have the same meaning as in formula (1).

The monoadduct of formula (5) is obtained by purification:

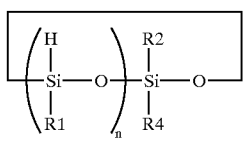
(5)

with the proviso that the radicals $R^1$, $R^2$ and $R^4$ have the same meaning as in formula (1).

The representatives of the general formula (5) are prepared by catalytic reaction with compounds of formula (4) which contain at least one C=C double bond. The compounds according to formula (3) are introduced in suitable solvents, for example toluene, and reacted with the stoichiometric amount of the representative of formula (4). Particularly preferred representatives of (3) contain three to five siloxane units, such as 1,3,5,7-tetramethylcyclotetrasiloxane, 1,3,5,7-tetraethylcyclotetrasiloxane, 1,3,5,7-tetraphenylcyclotetrasiloxane, 1,3,5,7,9-pentamethylcyclopentasiloxane, 1,3,5,7,9-pentaethylcyclopentasiloxane, and 1,3,5,7,9-pentaphenylcyclopentasiloxane. Particularly suitable representatives of formula (4) are vinyl- or allyltrialkylsilanes, such as vinyltrimethoxysilane (Wacker), allyltrimethoxysilane, vinyltriethoxysilane and allyltriethoxysilane.

Representatives of the general formula (1) are finally prepared by catalytic reaction of compounds according to formula (5) with compounds of formula (6)

$$R^{12}-Z \qquad (6)$$

where $R^{12}$ has the same meaning as in formula (4) and Z the same meaning as in formula (1).

Suitable catalysts are homogeneous and heterogeneous precious-metal catalysts, particularly homogenous and heterogeneous platinum catalysts, quite particularly Speier catalyst, Karstedt catalyst, platinum on active carbon, Wilkinson catalyst, Deloxan catalyst (Degussa), polymer-bound Wilkinson catalyst, platinum on aluminum oxide and platinum on barium sulfate.

The following substances according to the general formula (1) are explicitly a subject of the invention, and in each case the ethyl-substituted variants (—Si(OEt)$_3$) are also to count as part of the invention:
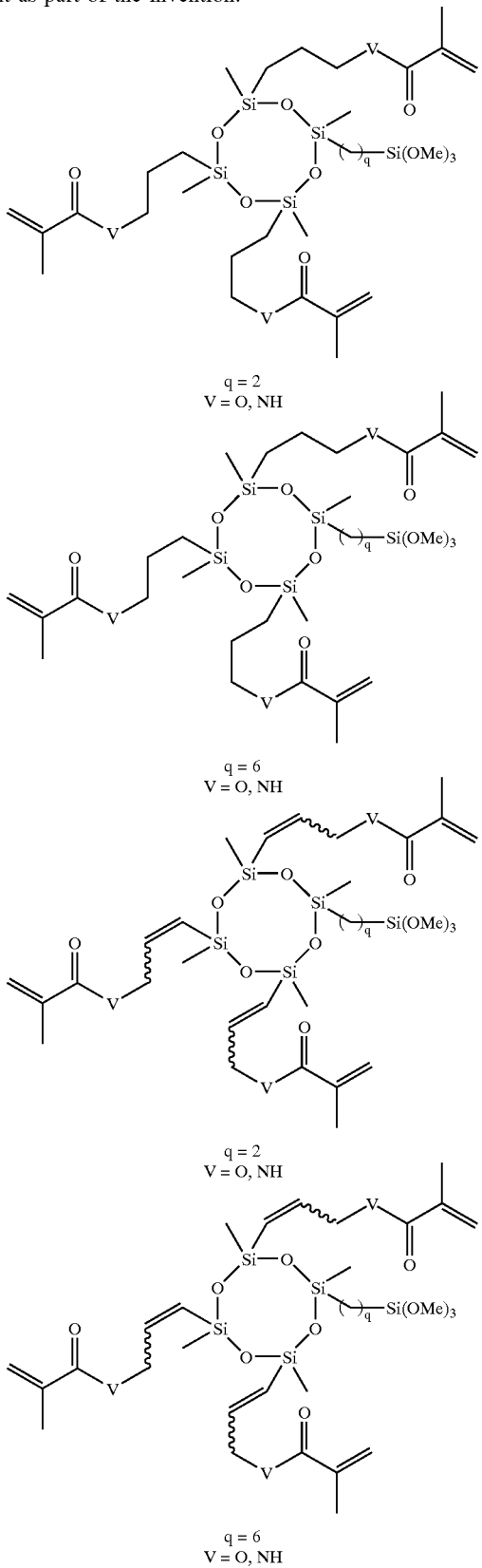
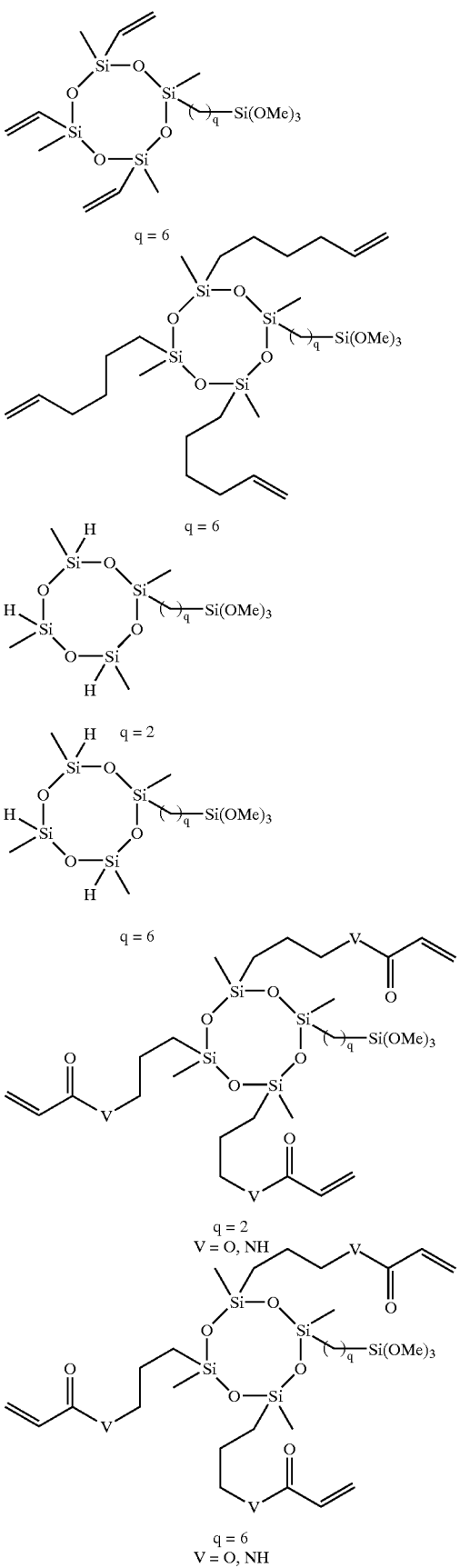

-continued
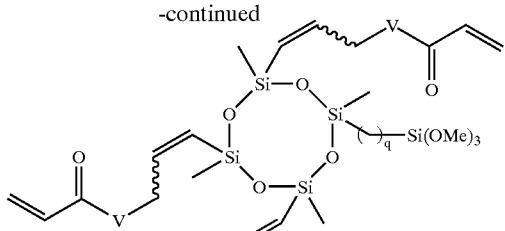
q = 2
V = O, NH
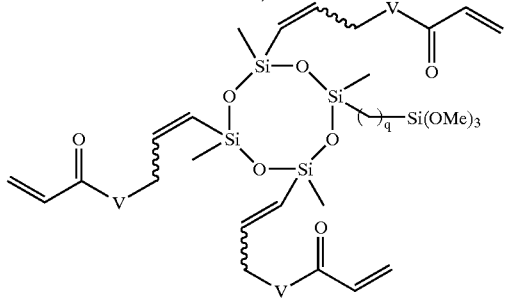
q = 6
V = O, NH
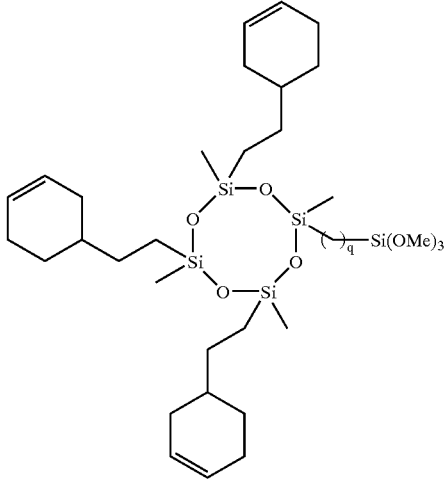
q = 2
q = 6
-continued
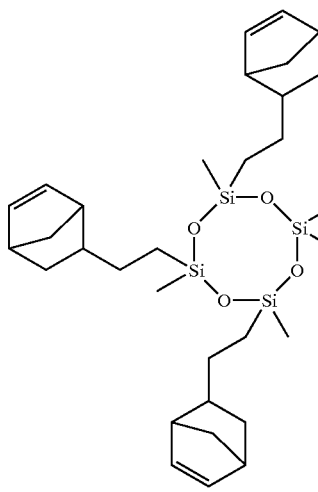
q = 2
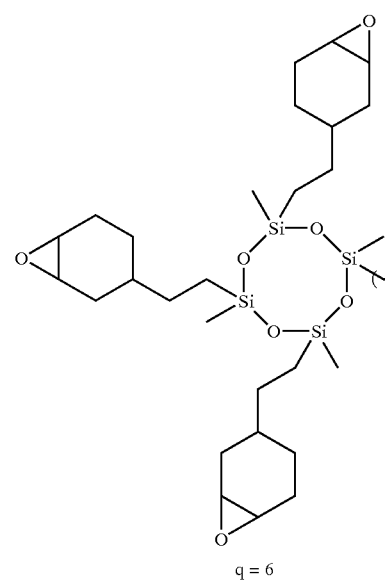
q = 6
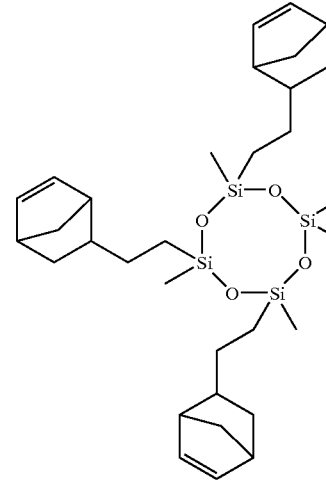
q = 6

-continued

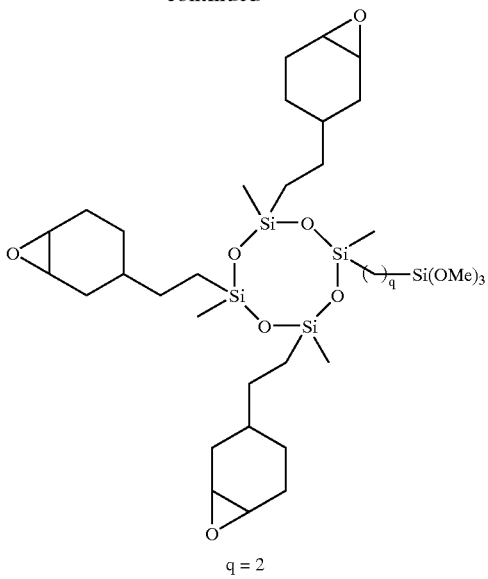

q = 2

The above formulae reproduce the idealized state of exclusively β-hydrosilylated products. The compounds actually also contain a proportion of α-adducts, as is known from the literature to occur in every hydrosilylisation.

For the preparation of sol-gel-condensed resins, representatives of formula (1) are hydrolyzed in principle with water. For condensates the individual monomers are hydrolyzed separately, combined and condensed together.

If silicon compounds are used almost exclusively, the hydrolytic condensation can take place in most cases by adding to the hydrolyzing silicon compounds, which are present either as such or dissolved in a suitable solvent, the stoichiometrically required amount of water or optionally an excess of water at room temperature or with slight cooling direct—preferably with stirring and in the presence of a suitable hydrolysis and condensation catalyst. The mixture thus resulting is stirred for some time—up to several hours.

In the presence of more reactive compounds (Ti, Al, Zr), a stepwise addition of the water is recommended as a rule.

Regardless of the reactivity of the compounds used, the hydrolysis takes place as a rule at temperatures between −20° C. and 130° C., preferably between 0 and 30° C. or at the boiling point of the optionally used solvent.

Because of the different reactivities of the compounds, it may be expedient to introduce the water first and add the dissolved compounds, introduce the dissolved compounds first and add the water, add or introduce the water in the form of hydrous organic or inorganic solvents, or incorporate the water into the reaction mixture in the form of moisture-laden adsorbents, such as molecular screens. The water can also be added via a reaction in which water is formed, for example during ester formation from acid and alcohol.

In order to counter precipitations during the hydrolysis, it has proved to be expedient to add the water in several steps or in drops.

If a solvent is used consideration can also be given, in addition to the low aliphatic alcohols (e.g. ethanol, isopropanol), to ketones, for example low dialkyl ketones, such as acetone and methyl isobutyl ketone, ethers, for example low dialkyl ethers, such as diethyl ether and dibutyl ether, THF, amides, esters, for example ethyl acetate, dimethylformamide, and their mixtures.

If hydrolysis and condensation catalysts are to be used, compounds which split off protons are preferred. Examples of these are organic and inorganic acids, such as hydrochloric acid, formic acid and acetic acid. In the case of a basic catalysis, $NH_3$, NaOH or KOH for example are suitable. A catalysis with fluoride ions is also possible, for example using KF, HF or $NH_4F$.

Among the hydrolytically condensable compounds different from siloxanes of the general formula (1) which can be optionally used, according to component A2 those of formula (2) and according to component A3 those of the following general formula (7) are particularly preferred:

$$X_{a'}SiR^{13}_{b'}$$

Here, X is as defined before, a' represents an integer from 1 to 4, in particular 2 to 4 and b' 0, 1, 2 or 3, preferably 0, 1 or 2. $R^{13}$ represents alkyl, alkenyl, aryl, alkylaryl, or arylalkyl radicals, as defined above.

Particularly preferred compounds of the general formula (7) are those in which the radicals X, which can be the same or different, are selected from halogen (F, Cl, Br and i, in particular Cl and Br) alkoxy (in particular $C_1$–$C_4$ alkoxy, such as e.g. methoxy, ethoxy, n-propoxy, i-propoxy and butoxy), aryloxy (in particular $C_6$–$C_{10}$ aryloxy, e.g. phenoxy), acyloxy (in particular $C_1$–$C_4$ acyloxy, such as e.g. acetoxy and propionyloxy) and hydroxy, the radicals R, which can be the same or different, are selected from alkyl (in particular $C_1$ to $C_4$ alkyl, such as e.g. methyl, ethyl, propyl and butyl), alkenyl (in particular $C_2$ alkenyl, such as e.g. vinyl, 1-propenyl, 2-propenyl and butenyl), alkinyl (in particular $C_2$–$C_4$ alkinyl, such as acetylenyl and propargyl) and aryl (in particular $C_6$–$C_{10}$ aryl, such as e.g. phenyl and naphthyl), the just-named groups (with the exception of halogen and hydroxy) optionally being able to contain one or more substituents which are inert under the reaction conditions, such as e.g. halogen and alkoxy. The above alkyl radicals also include the corresponding cyclic and aryl-substituted radicals, such as e.g. cyclohexyl and benzyl, while the alkenyl and alkinyl groups can also be cyclic and the named aryl groups are also to include alkaryl groups (such as tolyl and xylyl).

Along with the above-named particularly preferred X radicals, further, likewise suitable groups can also be named: hydrogen and alkoxy radicals with 5 to 20, in particular 5 to 10 carbon atoms and halogen- and alkoxy-substituted alkoxy groups (such as β-methoxyethoxy). Further suitable R groups are linear, branched or cyclic alkyl, alkenyl, and alkinyl radicals with 5 to 20, in particular 5 to 10 carbon atoms, such as e.g. n-pentyl, n-hexyl, dodecyl and octadecyl, as well as groups which have epoxy, mercapto or amino radicals.

The following applies both for the compounds of general formula (1) and those of the general formulae (2) and (7): As the radicals X are not present in the end-product, but are lost through hydrolysis, the hydrolysis product also having to be removed as a rule earlier or later in any suitable way, radicals X are particularly preferred which carry no substituent and lead to hydrolysis products with low molecular weight, such as e.g. low alcohols, such as methanol, ethanol, propanol, n-, i-, sec.- and tert.-butanol.

The compounds of the formulae (1), (2) and (7) can be used wholly or partly in the form of precondensates, i.e. compounds which have arisen through partial hydrolysis of the compounds of formulae (1), (2) and (7), either alone or mixed with other hydrolyzable compounds such as are described in more detail below. Such oligomers, preferably soluble in the reaction medium, can be linear or cyclic, low-molecular-weight part-condensates (polyorganosiloxanes) with a degree of condensation of e.g. approx 2 to 100 (e.g. 2 to 20), in particular approx 6 to 10.

Concrete examples of compounds (for the most part available in the trade) of the general formula (7) which are preferably used according to the invention are compounds of the following formulae:

Si(OCH$_3$)$_4$, Si(OC$_2$H$_5$)$_4$, Si(O—n— or i—C$_3$H$_7$)$_4$,

Si(OC$_4$H$_9$)$_4$, SiCl$_4$, HSiCl$_3$, Si(OOCCH$_3$)$_4$,

CH$_3$—SiCl$_3$, CH$_3$—Si(OC$_2$H$_5$)$_3$, C$_2$H$_5$—SiCl$_3$, C$_2$H$_5$—Si(OC$_2$H$_5$)$_3$,

C$_3$H$_7$—Si(OCH$_3$)$_3$, C$_6$H$_5$—Si(OCH$_3$)$_3$, C$_6$H$_5$—Si(OC$_2$H$_5$)$_3$, (CH$_3$O)$_3$Si—C$_3$H$_6$—Cl, (CH$_3$)$_2$SiCl$_2$, (CH$_3$)$_2$Si(OCH$_3$)$_2$, (CH$_3$)$_2$Si(OC$_2$H$_5$)$_2$, (CH$_3$)$_2$Si(OH)$_2$,(C$_6$H$_5$)$_2$SiCl$_2$, (C$_6$H$_5$)$_2$Si(OCH$_3$)$_2$, (C$_6$H$_5$)$_2$Si(OC$_2$H$_5$)$_2$, (i—C$_3$H$_7$)$_3$SiOH,

CH$_2$=CH—Si(OOCCH$_3$)$_3$,

CH$_2$=CH—SiCl$_3$, CH$_2$=CH—Si(OCH$_3$)$_3$, CH$_2$=CH—Si(OC$_2$H$_5$)$_3$,

CH$_2$=CH—Si(OC$_2$H$_4$OCH$_3$)$_3$, CH$_2$=CH—CH$_2$—Si(OCH$_3$)$_3$,

CH$_2$=CH—CH$_2$—Si(OC$_2$H$_5$)$_3$,

CH$_2$=CH—CH$_2$—Si(OOCCH$_3$)$_3$,

CH$_2$=C(CH$_3$)—COO—C$_3$H$_7$—Si(OCH$_3$)$_3$,

CH$_2$=C(CH$_3$)—COO—C$_3$H$_7$—Si(OC$_2$H$_5$)$_3$, (C$_2$H$_5$O)$_3$Si—C$_6$H$_4$—NH$_2$, CH$_3$(C$_2$H$_5$O)$_2$Si—(CH$_2$)$_4$—N H$_2$, (C$_2$H$_5$O)$_3$Si—C$_3$H$_6$—NH$_2$, (CH$_3$)$_2$(C$_2$H$_5$O)Si—CH$_2$—NH$_2$, (C$_2$H$_5$O)$_3$Si—C$_3$H$_6$—CN, (CH$_3$O)$_3$Si—C$_4$H$_8$—SH, (CH$_3$O)$_3$Si—C$_6$H$_{12}$—SH, (CH$_3$O)$_3$Si—C$_3$H$_6$—SH, (C$_2$H$_5$O)$_3$Si—C$_3$H$_6$—SH, (CH$_3$O)$_3$Si—C$_3$H$_6$—NH—C$_2$H$_4$—NH$_2$, (CH$_3$O)$_3$Si—C$_3$H$_6$—NH—C$_2$H$_4$—NH—C$_2$H$_4$—NH$_2$.

These silanes can be prepared according to known methods; compare W. Noll, "Chemie und Technologie der Silicone", Verlag Chemie GmbH, Weinheim/Bergstraße (1968).

The proportion of the silicon compounds with four, three, two or one hydrolyzable radical X (or also of the hydrolyzable compounds different from silicon compounds) relative to one another is based above all on the desired properties of the resulting polycondensate or of the end-product prepared from them.

Among the hydrolyzable aluminium compounds according to components A3 optionally used for the preparation of the polycondensates, those are particularly preferred which have the general formula (8):

$$AlX'_3 \qquad (8)$$

in which the X' radicals, which can be the same or different, are selected from halogen, alkoxy, alkoxycarbonyl and hydroxy. With regard to the more detailed (preferred) definition of these radicals, reference can be made to the statements in connection with hydrolyzable silicon compounds suitable according to the invention. The just-named groups can be wholly or partly replaced by chelate ligands (e.g. acetylacetone or ethyl acetoacetate, acetic acid).

Particularly preferred aluminium compounds are the aluminium alkoxides and halides. In this connection, the following can be named as concrete examples:

Al(OCH)$_3$, Al(OC$_2$H$_5$)$_3$, Al(O—n—C$_3$H$_7$)$_3$, Al(O—i—C$_3$H$_7$)$_3$, Al(OC$_4$H$_9$)$_3$, Al(O—i—C$_4$H$_9$)$_3$, Al(O—sec—C$_4$H$_9$)$_3$, AlCl$_3$, AlCl(OH)$_2$.

Compounds which are liquid at room temperature, such as e.g. aluminium-sec-butylate and aluminium isopropylate, are particularly preferred.

Suitable hydrolyzable titanium and zirconium compounds according to component A3 which can be used according to the invention are those of the following general formula (9):

$$MX_{a'}R^{13}_{b'} \qquad (9)$$

in which M means Ti or Zr and X, R$^{13}$, a' and b' are defined as in the case of the general formula (7). This also applies to the preferred meanings of X and R. Particularly preferably, the compounds of formula (9) are those in which a' is equal to 4.

As in the case of the above A1 compounds, complexed Ti- and Zr compounds can also be used. Additional preferred complexing agents are acrylic acid and methylacrylic acid here.

Concrete examples of zirconium and titanium compounds that can be used according to the invention are the following:

TiCl$_4$, Ti(OC$_2$H$_5$)$_4$, Ti(OC$_3$H$_7$)$_4$, Ti(O—i—C$_3$H$_7$)$_4$, Ti(OC$_4$H$_9$)$_4$, Ti(2-ethylhexoxy)$_4$, ZrCl$_4$, Zr(OC$_2$H$_5$)$_4$, Zr(OC$_3$H$_7$)$_4$, Zr(O—i—C$_3$H$_7$)$_4$. Zr(OC$_4$H$_9$)$_4$, ZrOCl$_2$, Zr(2-ethylhexoxy)$_4$.

Further hydrolyzable compounds which can be used for the preparation of the polycondensates according to the invention are e.g. boron trihalides and boric acid esters (such as e.g. BCl$_3$, B(OCH$_3$)$_3$ and B(OC$_2$H$_5$)$_3$), tin tetrahalides and tin tetraalkoxides (such as e.g. SnCl$_4$ and Sn(OCH$_3$)$_4$) and vanadyl compounds, such as e.g. VOCl$_3$ and VO(OCH$_3$)$_3$.

A further subject of the invention are dental compositions which are based on the substances according to the invention. They contain for example:

(A) 0.1 to 40, preferably 5 to 15 parts by mass cyclic sol-gel-condensable siloxanes according to the invention according to formula (1) or their co-condensates described above, (B) 0 to 20, preferably 5 to 15 parts by mass co-monomers, (C) 40 to 90, preferably 75 to 88 parts by mass fine-particled inorganic and/or organic filling substances, (D) 0.1 to 5 parts by mass an initiator system which is capable of forming free radicals, (E) 0 to 20 parts by mass modifiers, such as thixotropic agents, dyes, stabilizers, where the sum of parts by mass is 100.

If a curing of the polycondensates according to the invention by irradiation (UV or IR radiation) and/or thermal energy is intended, then a suitable initiator can be added as component (D). The polycondensates according to the invention can however also be cured on their own using such an initiator system.

The photoinitiators available in the trade can be used for example. Examples of these are Irgacure 184 (1-hydroxycyclohexylphenyl ketone), Irgacure 500 (1-hydroxycyclohexylphenyl ketone, benzophenone) and other Irgacure-type photoinitiators available from Giba-Geigy; Darocur 1173, 1116, 1398, 1174 and 1020 (available from Merck), benzophenone, 2-chlorothioxanthone, 2-methylthioxanthone, 2-isopropylthioxanthone, benzoin, 4,4'-dimethoxybenzoin, benzoin ethyl ether, benzoin isopropyl ether, benzyldimethyl ketal, 1,1,-trichloroacetophenone, diethoxyacetophenone, dibenzosuberone and camphorquinone. The last-named initiator is particularly suitable when irradiating with light in the visible spectrum.

Organic peroxides in the form of diacyl peroxides, peroxydicarbonates, alkylperesters, dialkyl peroxides, perketals, ketone peroxides and alkylhydroperoxides can be considered in particular as thermal initiators. Concrete and preferred examples of thermal initiators are dibenzoyl peroxide, tert.-butyl perbenzoate as well as azobisisobutyrontrile. The initiator can be added in normal amounts. Thus e.g. initiator can be added, to a mixture which contains 30 to 50 percent by weight polycondensate, in an amount of e.g. 0.5 to 5 percent by weight, in particular 1 to 3 percent by weight, relative to the mixture.

The curing is dependent on the type or presence of an initiator, and can be carried out thermally or by irradiation (e.g. with a UV radiator, a laser, an electron beam, a light source, which emits radiation in the visible spectrum) in a manner known per se. Obviously, combinations of curing methods are also possible, e.g. UV/IR or UV/thermal.

Inorganic, but also organic polymeric fillers are as a rule suitable as fillers According to component (C). Quartz, ground glasses, silica gels as well as pyrogenic silicic acids and precipitation silicic acids or their granules can be cited as examples. X-ray-opaque fillers are also preferably used, at least partially. These can for example be X-ray-opaque glasses, that is to say glasses which for example contain strontium, barium or lanthanum (e.g. according to U.S. Pat. No. 3,971,754) some of the fillers can also consist of an X-ray-opaque additive, such as for example yttrium trifluoride, strontium hexafluorozirconate or fluorides of the rare earth metals (e.g. according to EP-A-0 238 025). For better incorporation into the polymer matrix, it is advantageous to hydrophobize the inorganic fillers. Customary hydrophibization agents are silanes, for example trimethoxymethacryloyloxypropyl silane or trimethoxyglycidyl silane.

The fillers preferably have an average grain size <20µm and in particular <5 µm and an upper grain limit of 150, preferably 70 µm and in particular 25 µm. Particularly preferably, mixtures of 5 to 25% wt.-% fillers with an average grain size of 0.02 to 0.06 µm and 65 to 85% fillers with an average grain size of 1 to 5 µm are used.

Suitable auxiliaries and additives according to component (E) can for example normally be stabilizers, pigments or thinning agents used in the field of dentistry.

Co-monomers according to component (B) are at least singly ethylenically unsaturated. Preferably used ethylenically unsaturated co-monomers are acrylates or methacrylates. Mono- and polyfunctional (meth)acrylate monomers are generally suitable. Typical representatives of this class of compounds (P 43 28 960.6) are alkyl(meth)acrylates, including the cycloalkyl(meth)acrylates, aralkyl(meth)acrylates and 2-hydroxyalkyl(meth)acrylates, for example hydroxypropyl methacrylate, hydroxyethyl meth-acrylate, isobornyl acrylate, isobornyl methacrylate, butyl glycol methacrylate, acetyl glycol methacrylate, triethylene glycol dimethacrylate, polyethylene glycol dimethacrylate, 2-phenyl-ethyl methacrylate, 2-ethylhexyl methacrylate, cyclohexyl methacrylate, lauryl methacrylate and hexanedioldi(meth)acrylate. Long-chained monomers of U.S. Pat. No. 3,066,112 based on Bisphenol A and glycidyl methacrylate or their derivatives resulting from addition of isocyanates can also be used. Compounds of the bisphenyl-A-diethyloxy(meth)acrylate and bisphenol-A-dipropyloxy (meth)acrylate type are also suitable. The oligoethoxylated and oligopropoxylated bisphenol-A dicacrylic and dimethacrylic acid esters can also be used. The diacrylic and dimethacrylic acid esters of bis(hydroxymethyl)tricyclo [5.2.1.0$^{2.6}$]decane named in DE-C-28 16 823 and the diacrylic and dimethacrylic acid esters of the compounds of Bis(hydroxymethyl)-tricyclo[5.2.1.0$^{2.6}$]-decane extended with 1 to 3 ethylene oxide and/or propylene oxide units are also well suited.

The preparation process of the dental compositions disclosed here is preferably such that the liquid constituents are mixed with one another, the initiators, if they are not liquid, are dissolved therein by stirring and the fillers are then added and well homogenized by kneading.

Two-component preparations which are cured by redox mechanisms are formulated such that the essential constituents of the redox initiation system are each introduced separately into a part of the two-component preparation. The distribution of the constituents of the overall preparation is based on the relevant storage properties and the desired mixing ratio.

The following examples explain the invention, without its intending to be limited thereby.

Preparation of a Representative of (5) 1 - (Trimethoxysilylethyl)-1,3,5,7-tetramethylcyclotetrasiloxane (V1)

962 g of 1,3,5,7-tetramethylcyclotetrasiloxane are introduced in 800 ml of toluene with a Karstedt catalyst (3–3.5% Pt, 300 ppm Pt, ABCR) and stirred at 70° C. 296.4 g of vinyltrimethoxysilane (Wacker) is added dropwise within five hours. After a further 24 hours of stirring, the mixture undergoes fractional distillation.

Preparation of Representatives of (1) 1 - (Trimethoxysilylethyl)-3,5,7-tris(3-methacryloxypropyl)-1,3,5,7-tetramethylcyclotetrasiloxane 47.3 g of allyl methacrylate and 100 ml of toluene are dissolved and heated with a Karstedt catalyst (3–3.5% Pt, 300 ppm Pt, ABCR) to 70° C. 38.9 g (V1) are added dropwise within 3 hours. After a further 12 hours of stirring the solvent is distilled off.

1-(Trimethoxysilylethyl)-3,5,7-tris(5-hexenyl)-1,3,5,7-tetramethylcyclotetrasiloxane 52.3 g 1,6-hexadiene are dissolved in 100 ml toluene and heated with a Karstedt catalyst (3–3.5 % Pt, 300 ppm Pt, ABCR) to 70° C. 27.5 g (V1) are added dropwise within 3 hours. After a further 12 hours of stirring the solvent and the excess hexadiene is distilled off. The product undergoes fractional distillation.

1-(Trimethoxysilylethyl)-3,5,7-tris(3-ethylene-oxabicyclo[4.1.0]heptane)yl)-1,3,5,7-tetramethylcyclotetrasiloxane 24.5 vinylcyclohexene epoxide are dissolved in 100 mm toluene and heated with a Karstedt catalyst (3–3.5% Pt, 300 ppm Pt, ABCR) to 70° C. 25.6 g (V1) are added dropwise within three hours. After a further 12 hours of stirring the solvent is distilled off.

Preparation of a Resinous Composition

A solution of (V1) in diethyl ether is hydrolyzed with 1.5 mol per mol (V1) water (used as 0.1 n HCl) per mol silane and condensed. Then the ether solution is washed with small portions of water until the neutral point. After the drying of the solution, the solvent is drawn off and the remaining viscous residue is dried in high-vacuum.

Preparation of the Dental Preparations

For the preparation of the dental preparations according to the invention, the organic/inorganic prepolymers characterized in Table 1 were used.

TABLE 1

Summary of the organic/inorganic prepolymers used according to the invention

| OAP No. | Structural formula/designation | Viscosity [Pas] | Double bond equivalent [g] |
|---|---|---|---|
| 1 | Hydrolysate/condensate from: 1-(trimethoxysilylethyl)-3,5,7-tris(3-methacryloxypropyl)-1,3,5,7-tetramethylcyclotetrasiloxane | 3 | 270 |
| 2 | Hydrolysate/condensate from: 1-(trimethoxysilylethyl-3,5,7-tris(3-methacryloxypropyl)-1,3,5,7-tetramethylcyclotetrasiloxane | 95 | 250 |
| 3 | SiO$_2$ co-condensate | 15 | 300 |

TABLE 1-continued

Summary of the organic/inorganic prepolymers used according to the invention

| OAP No. | Structural formula/designation | Viscosity [Pas] | Double bond equivalent [g] |
|---|---|---|---|
| 4 | Co-hydrolysate/condensate from: 1-(trimethoxysilylethyl)-3,5,7-tris(3-methacryloxypropyl)-1,3,5,7-tetramethylcyclotetrasiloxane and tetramethoxysilane Co-condensate from compounds VC1 and VC2 Co-hydrolysate/condensate from: 1-(trimethoxysilylethyl)-3,5,7-tris(3-methacryloxypropyl)-1,3,5,7-tetramethylcyclotetrasiloxane and 2,2-[bis-(4-hydroxyphenyl)-propane-4-methacrylate-4'-(3-trimethoxysilyl-1-carbamate) | 24 | 410 |

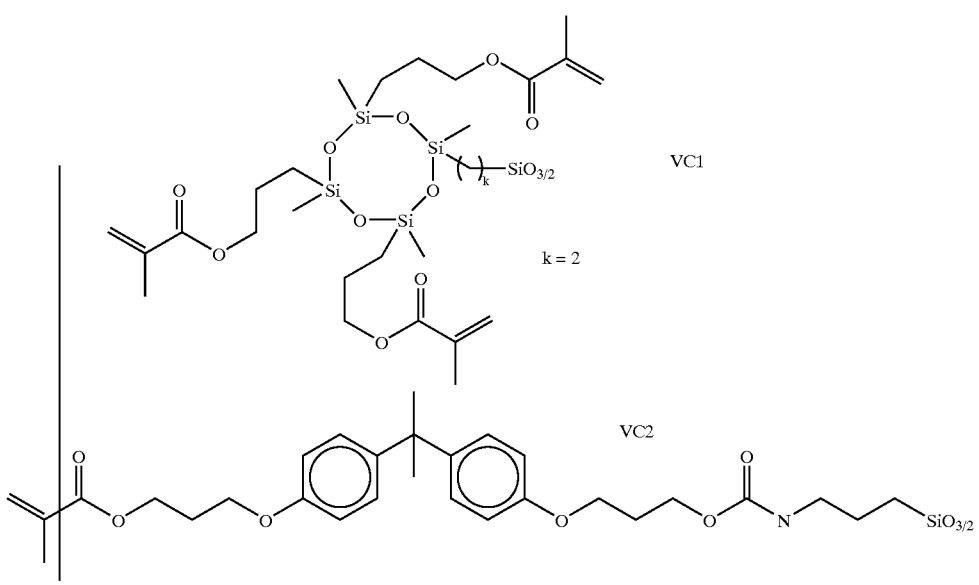

VC1, k = 2

VC2

| 5 | Co-condensate from compounds VC3 and VC4 Co-hydrolysate/condensate from: 1-(trimethoxysilylethyl)-3,5,7-tris(3-methacryloxypropyl)-1,3,5,7-tetramethylcyclotetrasiloxane and bis-(hydroxymethyl)-tricyclo[5.2.1.0$^{2.6}$]decane-methacrylate-(3-trimethoxysilyl-1-carbamate | 18 | 340 |

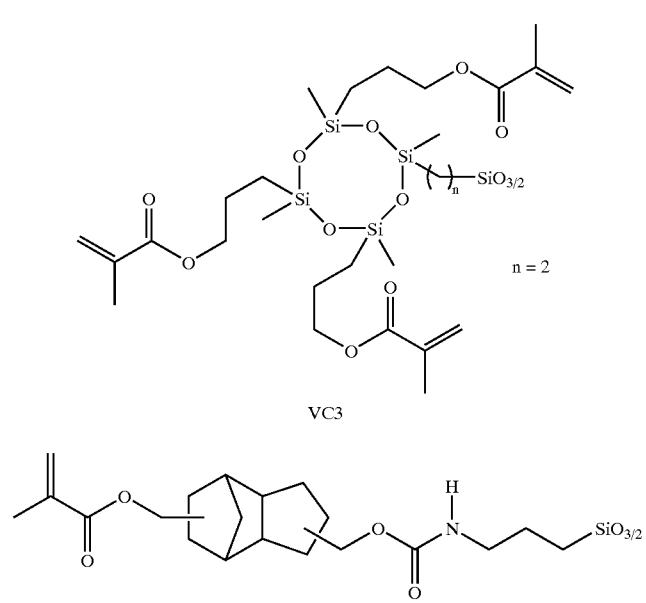

VC3, n = 2

VC4

The pasty preparations according to the patent examples 1 to 9, the compositions of which are described in Table 2, were prepared in a 100-ml laboratory kneader.

The compressive and bending strengths and the E-modulus of the preparations were characterized according to DIN ISO 4049.

The testpieces were prepared by 40 seconds' irradiation of the pasty preparations introduced into moulds using the Elipar II light apparatus from ESPE Dental AG, Germany.

Following removal from the mould, the testpieces were stored in deionized water at 36° C. for a period of 24 hours, after which the mechanical properties were ascertained.

The volume shrinkage occurring during the radical polymerization was established by measuring the densities of the pasty preparations and of the cured compositions, using the buoyancy method.

Table 3 contains a summary of the property values ascertained for the cured preparations according to the invention examples 1 to 9.

COMPARISON EXAMPLE 1

The preparation and characterization of the comparison preparation is carried out as described above in the patent examples.

Table 2 contains the composition of the pasty preparations according to the comparison example. The results of the ascertainment of the property values are contained in Table 3. The preparations according to the invention show, vis-a-vis the comparison preparation, a clearly decreased volume shrinkage for approximately the same mechanical strength values.

TABLE 2

Composition of the pasty preparations according to the patent examples 1 to 9 and comparison example 1

| Constituent | Comparison example 1 | Patent examples No. 1 | 2 | 3 | 4 | 5 | 6 | 7 | 8 | 9 |
|---|---|---|---|---|---|---|---|---|---|---|
| | | | | | Proportions in wt.-% | | | | | |
| Organic-/inorganic prepolymer as per Table 1 | | | | | | | | | | |
| OAP 1 | ... | 8.33 | 2.73 | 1.82 | 3.57 | 6.13 | ... | ... | ... | 3.47 |
| OAP 2 | ... | ... | 5.56 | 3.78 | 1.27 | ... | 7.81 | 7.31 | 9.23 | 1.73 |
| OAP 3 | ... | ... | ... | 4.3 | ... | ... | 1.73 | 1.02 | ... | 2.74 |
| OAP 4 | ... | ... | ... | ... | 3.42 | ... | 1.31 | ... | 0.71 | 0.79 |
| OAP 5 | ... | ... | ... | ... | ... | 4.37 | ... | 2.73 | ... | ... |
| Quartz powder, average particle size 1.5 micrometers, silanized | 46.13 | 79.3 | 81.2 | 48.7 | 81.7 | 48.8 | 70.7 | 77.7 | 79.81 | 6.7 |
| Strontium silicate glass, average particle size 1.2 micrometers, silanized | 30.17 | ... | ... | 30.1 | ... | 30.7 | 10.08 | ... | ... | 73.07 |
| 2,2-Bis-4(3-hydroxypropoxyphenyl)-propane-dimethacrylate | 7.51 | 6.92 | ... | ... | 2.99 | ... | 3.04 | ... | ... | ... |
| 2,2-Bis-4(2-hydroxypropoxyphenyl)-propane-dimethacrylate | ... | ... | ... | ... | ... | 7.12 | ... | ... | ... | 5.22 |
| 7,7,9-trimethyl-4,13-dioxo-3,14-dioxa-5,12-diaza-hexadecane-1,16-diolimethacrylate | ... | 3.74 | ... | 10.82 | ... | ... | ... | 6.73 | 9.87 | 3.07 |
| 2,2-Bis-4(2-hydroxyethoxyphenyl)propanebis-methacrylate | ... | 1.27 | ... | ... | ... | ... | 1.37 | 4.13 | ... | ... |
| Bis-acryloyloxymethyltricyclo[5.2.1.0$^{2,6}$]-decane | 15.71 | ... | 10.13 | ... | 6.61 | 2.43 | 3.56 | ... | ... | 2.74 |
| 2,2'-(3-methoxypropylnitrilo)diethanoldi-methacrylate | 0.41 | 0.36 | 0.32 | 0.41 | 0.38 | 0.37 | 0.32 | 0.31 | 0.39 | 0.41 |
| 1,7,7-trimethyl-bicyclo-[2,2,1]-heptanedion-2,3 | 0.07 | 0.08 | 0.06 | 0.07 | 0.06 | 0.08 | 0.08 | 0.07 | 0.09 | 0.06 |

TABLE 3

Summary of the property values, ascertained for the cured preparations according to the patent examples 1 to 9 and comparison example 1 (Table 2)

| Property | Comparison example 1 | Patent examples No. 1 | 2 | 3 | 4 | 5 | 6 | 7 | 8 | 9 |
|---|---|---|---|---|---|---|---|---|---|---|
| Compressive strength/Mpa | 423 | 422 | 435 | 417 | 442 | 445 | 427 | 418 | 401 | 419 |
| Bending strength/Mpa DIN ISO 4049 | 115 | 102 | 112 | 107 | 119 | 121 | 117 | 109 | 116 | 117 |
| Elasticity modulus/Mpa | 8312 | 8273 | 8083 | 7317 | 7918 | 8132 | 8615 | 7613 | 7513 | 7916 |
| Volume shrinkage/% using the buoyancy method | 3.49 | 2.42 | 2.27 | 2.57 | 2.21 | 2.29 | 2.51 | 2.31 | 2.19 | 2.24 |

What is claimed is:

1. Polysiloxanes obtainable by sol-gel-condensation of A1, 60 to 100 mol % relative to the condensate from A1, A2 and A3, monomers or precondensates of sol-gel condensable cyclic siloxanes of the general formula (1):

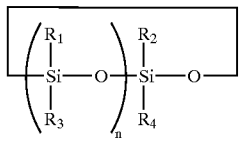 (1)

in which the following mean:
- $R^1, R^2$: alkyl with 1 to 10 C atoms, alkenyl with 2 to 10 C atoms, fluoroalkyl with 1 to 10 C atoms, cycloalkyl with 3 to 12 C atoms, aryl with 6 to 18 C atoms,
- $R^3$: $R^5$—Z
- $R^4$: $R^6$—(A—$R^6$)$_c$—SiX$_a$R$^7{}_b$,
- $R^5, R^6$: alkylene linear or branched with 2 to 10 C atoms, alkenylene linear or branched with 1 to 10 C atoms, cycloalkylene with 3 to 12 C atoms, cycloalkenylene with 3 to 12 C atoms, alkarylene with 6 to 18 C atoms with up to 3 heteroatoms selected from the group consisting of O, N, and S,
- $R^7$: alkyl with 1 to 10 C atoms, alkenyl with 2 to 10 C atoms, aryl with 6 to 18 C atoms, alkylaryl with 6 to 24 C atoms, arylalkyl with 6 to 24 C atoms,
- Z: a linear, branched or cyclic organic radical with at least one C=C double bond or at least one epoxide function and at least 4 to 50 carbon atoms and up to 10 heteroatoms selected from the group consisting of O, N and S,
- A: O, S, NHC(O)O, NHC(O)NR$^8$, OC(O)NH, OC(O), or C(O)O,
- X: H, halogen, hydroxy, acyloxy, alkylcarbonyl, NR$^8{}_2$, alkoxy, alkoxycarbonyl, the acyl, alkyl or alkoxy radicals containing 1 to 10 C atoms,
- $R^8$: H, alkyl with 1 to 10 C atoms, or aryl with 6 to 18 C atoms,
- n: 2 to 16,
- a: 1, 2 or 3,
- b: 0, 1 or 2,
- with the proviso that a+b=3, and
- c: 0 or 1, A2 0 to 40 mol %, relative to the condensate from A1, A2, and A3, of organic sol-gel-condensable monomers, and A3 0 to 40 mol %, relative to the condensate from A1, A2, and A3, of one or more sol-gel-condensable compounds of silicon and optionally other elements form the group selected from the group consisting of B, Al, P, Sn, Pb, the transition metals, the lanthanides and aktinides, where the sum of the amounts from A2 and A3 does not exceed 40 mol % and the amounts of A1, A2 and A3 must be made up to 100 mol %.

2. Polysiloxanes according to claim 1, obtainable through sol-gel condensation of 100 mol % of component A1.

3. Polysiloxanes, obtainable by sol-gel condensation of
A1 60 to 100 mol %, relative to the condensate from A1 and A2, monomers or precondensates of the sol-gel-condensable cyclic siloxanes according to claim 1 and
A2 0 to 40 mol %, relative to the condensate from A1 and A2 of organic sol-gel-condensable monomers, where the representatives of component A2 obey formula (2):

$$\{Y_eR_fSi[R'(B)_g]_{(4-e-f)}\}_xC \quad (2)$$

in which the radicals and indices have the following meaning:
- Y: hydrogen, halogen, hydroxy, alkoxy, acyloxy, alkylcarbonyl, alkoxycarbonyl or —NR″$_2$;
- R: alkyl, alkenyl, aryl, alkylaryl or arylalkyl;
- R′: alkylene, arylene or alkylenearylene:
- R″: hydrogen, alkyl or aryl;
- B: O, S, PR″, POR″, NHC(O)O or NHC(O)NR″;
- C: linear or branched or cyclic or polycyclic organic radical, which contains at least one C=C double bond, consists of 5 to 70 C atoms and contains 0 to 20 heteroatoms selected from the group consisting of O, N, and S;
- e: 1, 2 or 3;
- f: 0, 1 or 2;
- g: 0 or 1;
- x: an integer, the maximum value of which corresponds to the number of double bonds in C minus 1 or is equal to the number of double bonds in C, if g=1 and B stands for NHC(O)O or NHC(O)NR″.

4. Resins, obtainable by partial or complete hydrolysis of the groups X of representatives of the siloxanes according to claim 1 and subsequent partial or complete condensation with optional partial or complete saturation of the remaining Si—OH groups with $R^9R^{10}R^{11}$Si groups, $R^9$, $R^{10}$ and $R^{11}$ meaning the same or different alkenyl groups with 2 to 10, C atoms.

5. Co-condensates of the partially or completely hydrolyzed siloxanes according to claim 1 with representatives of A3.

6. Polycondensates according to claim 1 with hydrolyzable aluminium compounds according to component A3 according to the general formula (8):

 (8)

in which the radicals X′ which can be the same or different and are chosen from the group consisting of halogen, alkoxy, alkoxycarbonyl and hydroxy.

7. Polycondensates according to claims 1 or 5 with hydrolyzable titanium and zirconium compounds according to component A3 of the general formula (9):

 (9)

in which M means Ti or Zr and X, $R^{13}$, a′ and b′ are defined as in the case of the general formula (7)

 (7)

wherein
X is H, halogen, hydroxy, acyloxy, alkylcarbonyl, NR$^8{}_2$, alkoxy, alkoxycarbonyl, wherein the acyl, alkyl or alkoxy radicals contain 1 to 10 C atoms, a′ represents an integer from 1 to 4, and b′ is 0, 1, 2 or 3, $R^{13}$ represents alkyl, alkenyl, aryl, alkylaryl, or arylalkyl radicals, and $R^8$ represents H, alkyl with 1 to 10 C atoms or aryl with 6 to 18 C atoms.

8. Dental compositions containing
(A) 0.1 to 40 parts by mass polysiloxanes according to claim 1 and/or resins according to claim 4 and/or co-condensates according to claim 5,
(B) 0 to 20 parts by mass at least one co-monomer,
(C) 40 to 90 parts by mass fine-particled inorganic and/or organic fillers,
(D) 0.1 to 5 parts by mass an initiator system which is capable of forming free radicals, (E) 0 to 20 parts by mass modifiers, where the sum of the parts by mass is 100.

9. A method of preparing coating materials, adhesives and sealing compounds comprising incorporating the polysiloxanes according to claim 1.

10. A method of preparing coating materials, adhesives and sealing compounds comprising incorporating the polysiloxanes according to claim 2.

11. A method of preparing coating materials, adhesives and sealing compounds comprising incorporating the polysiloxanes according to claim 3.

12. The co-condensates according to claim 5 wherein A3 is an Si, Ti or Zr alkoxide and/or a substituted monoalkyltrialkoxysilanes.

* * * * *

UNITED STATES PATENT AND TRADEMARK OFFICE
CERTIFICATE OF CORRECTION

PATENT NO.      : 6,624,236 B1
DATED           : September 23, 2003
INVENTOR(S)     : Bissinger, Peter et al.

It is certified that error appears in the above-identified patent and that said Letters Patent is hereby corrected as shown below:

Column 2,
Line 67, delete "sol-gel condensation" and insert -- sol-gel-condensation --, therefor.

Column 3,
Line 51, delete "c." and insert -- c: --, therefor.
Line 64, delete "sol-gel condensation" and insert -- sol-gel-condensation --, therefor.

Column 4,
Line 37, delete "sol-gel condensation" and insert -- sol-gel-condensation --, therefor.
Line 51, delete "NR-$_2$" and insert -- NR"$_2$ --, therefor.

Column 5,
Line 33, delete "imethacryloyl" and insert -- dimethacryloyl --, therefor.

Column 6,
Line 30, after "1" delete ",".

Column 8,
Line 56, after "(6)" insert -- : --.

Column 15,
Line 62, delete "Particuarly" and insert -- Particularly --, therefor.

Column 16,
Line 22, after "$C_3H_7)_4$" delete "." and insert -- , --, therefor.

Column 17,
Line 15, delete "According" and insert -- according --, therefor.

Column 25,
Line 3, delete "sol-gel condensable" and insert -- sol-gel-condensable --, therefor.
Lines 49-50, after "elements" delete "form the group".
Lines 57 and 58, delete "sol-gel condensation" and insert -- sol-gel- condensation --, therefor.

UNITED STATES PATENT AND TRADEMARK OFFICE
CERTIFICATE OF CORRECTION

PATENT NO. : 6,624,236 B1
DATED : September 23, 2003
INVENTOR(S) : Bissinger, Peter et al.

It is certified that error appears in the above-identified patent and that said Letters Patent is hereby corrected as shown below:

<u>Column 26,</u>
Line 6, after "alkylenearylene" delete ":" and insert -- ; --, therefor.
Line 46, after "(7)" insert -- : --.

Signed and Sealed this

Twenty-seventh Day of September, 2005

JON W. DUDAS
*Director of the United States Patent and Trademark Office*